United States Patent [19]

Nishimura

[11] Patent Number: 5,105,354

[45] Date of Patent: Apr. 14, 1992

[54] METHOD AND APPARATUS FOR CORRELATING RESPIRATION AND HEARTBEAT VARIABILITY

[75] Inventor: Toshihiro Nishimura, Ooita, Japan

[73] Assignee: Nippon Kayaku Kabushiki Kaisha, Tokyo, Japan

[21] Appl. No.: 299,140

[22] Filed: Jan. 23, 1989

[51] Int. Cl.$^5$ .................... G06F 15/42; A61B 5/0205
[52] U.S. Cl. .................... 364/413.03; 364/413.06; 128/671
[58] Field of Search ............ 364/413.03, 413.06; 128/670, 671, 700, 702, 703, 706

[56] References Cited

U.S. PATENT DOCUMENTS

| | | | |
|---|---|---|---|
| 4,031,884 | 6/1977 | Henzel | 128/671 |
| 4,732,158 | 3/1988 | Sadeh | 128/702 |
| 4,862,361 | 8/1989 | Gordon et al. | 364/413.06 |
| 4,958,638 | 9/1990 | Sharpe et al. | 128/653 R |
| 4,958,640 | 9/1990 | Logan | 128/671 |
| 4,960,129 | 10/1990 | de Paola et al. | 128/695 |

OTHER PUBLICATIONS

Tomaselli et al., "Time Series Analysis of Periodic Components and Their Synchronization of Physiological Functions by Correlation Function and Power Spectrum", *Conference title: 3rd International Symposium on Biocybernertics*, German Dem. Republic, Aug. 3-7, 1971, (abstract only).

Penaz et al., "Spectral Analysis of Resting Variability of Some Circulatory Parameters", *Physiol Bohemsoslov*, vol. 27, No. 4, 1978, pp. 349-358, (abstract only).

Mulder et al., "Information Processing and Cardiovascular Control", *Psychophysiology*, vol. 18, No. 4, 1981, pp. 392-402.

Askelrod, "Power Spectrum Analysis of Heart Rate Fluctuation: A Quantitative Probe of Beat-to-Beat Cardiovascular Control", *Science*, vol. 213, Jul. 1981, pp. 220-222.

Gorden et al., "Abnormalities in Heart Rate and Respiratory Power Spectrum in Sudden Infant Death Syndrome", *Conference: Annual Meeting of the American Pediatric Society and the Society for Pediatric Research*, Washington, D.C., May 11-13, 1982, (abstract only).

Gorden et al., "Sudden Infant Death Syndrome: Abnormalities in Short Term Fluctuations in Heart Rate and Respiratory Activity", *Pediatric Research*, vol. 18, No. 10, 1984, pp. 921-926.

Weise et al., "Intercorrelation Analyses Among Age Spectral Parameters of Heart Rate Variability and Respiration in Human Volunteers", *J. Interdiscip. Cycle Res.*, 1990, pp. 17-24, (abstract only).

Zwiener et al., "Sleep State Related Dynamic of Neo Natal Heart Rate Fluctuations and Respiration Rhythms Within Several Frequency Ranges", *Automedica*, vol. 5, No. 1, 1984, pp. 77-90, (abstract only).

*Primary Examiner*—Dale M. Shaw
*Assistant Examiner*—David Huntley
*Attorney, Agent, or Firm*—Felfe & Lynch

[57] ABSTRACT

An evaluation method of respiration and heart beat and its apparatus which permits one to forecast sudden infant death syndrome by investigating correlation between respiration and heart beat in the normal state and sleep-apnea of a newborn.

2 Claims, 12 Drawing Sheets

METHOD AND APPARATUS FOR CORRELATING RESPIRATION AND HEARTBEAT VARIABILITY

BACKGROUND OF THE INVENTION

This invention relates to a method of evaluating data pertaining to respiration and heart beat and an apparatus for evaluating them, especially for forecasting sudden infant death syndrome (SIDS) by investigating the correlation between respiration and heart beat in a normal state and respiratory standstill in sleep.

Generally, the data from organisms includes EEG, cardiac electricity, respiration, ocular movement, and EMG. Signal forms of this data are relatively more useful than from EEG etc. It is therefore easier to analyze an R—R interval as a change of peak interval of an ECG wave, chronologically.

Considering that respiratory arrhythmia depends upon an efferent impulse from an extension receptor, standstill of the efferent impulse from an extension receptor in respiratory arrest in sleep will have an effect on heart beat. It has been already reported that in Cheyne Stokes respiration during hyperrespiration the increase of heart beat and decrease of blood pressure are observed; during its apnea the decrease of heart beat and increase of blood pressure occur.

Here, sleep-apnea syndrome is defined as three following cases:

(1) At least 30 episodes of apnea appear in the night sleep of 7 hours.

(2) An apnea episode appears in REM-sleep as well as in non-REM-sleep.

(3) An episode of apnea has a tendency to appear continuously.

The classification of sleep apnea syndrome according to Gastant is divided into the three following types (1) Central type: A respiratory standstill at the nostrils and mouth appears along with the disappearance of thoracid and abdominal movements. This indicates the stoppage of activity of the respiratory center.

(2) Obstructive or upper tracheal type: In spite of respiratory efforts by thracic and abdominal movements, respiration stops, suggesting an obstruction in the upper tracheal tract.

(3) Mixed type: An intermediate type between central and obstructive ones. Although at the first phase of apnea the thracic and abdominal movements cease, its symptom becomes more severe gradually.

In the central type, the apnea episode often appears repeatedly in an almost constant period, frequently observed in non-REM-sleep, but in the obstructive type an apnea episode appears at various intervals and its duration is also not constant. Also, in the central type, during hyperventilation in Cheyne Stokes respiration an increase of heart beat is observed. During the apnea phase its decrease and a periodical change are noticed.

The mechanism of the central type of sleep-apnea can be explained by neurogenous or respiratory disturbance theory. The neurogeneous theory is based on the assumption that there is an oscillation center in the brainstem, and an inhibitory mechanism for controlling oscillation in the forebrain. The respiratory disturbance theory rests on the basis that a respiratory disturbance delays a feed-back loop between the respiratory center and chemical receptor, and an oscillation phenomenon appears.

It has not been determined which effect really works, or whether both effects work simultaneously.

SUMMARY OF THE INVENTION

It has been reported that an apnea paroxysm relates to sudden infant death syndrome, etc., but correlation between respiration and heart beat is not fully elucidated. So far, the occurrence of apnea in a sleeping infant has been controlled by a respiratory monitor so that only the occurrence of the apnea episode can be detected, and the forecasting of this episode could not be allowed previously.

After this inventor studied the correlation between respiration and heart beat of infants, he found that the advancement of peak respiration rate to peak heart beat rate is several beats in the normal state, but from 5 to 6 minutes before the start of sleep-apnea this advancement changes to retardation or advancement of several tens beats, eminently, and came to this invention. The objects of this invention are the identification of the state just before the transition from normal to sleep-apnea in infants and the presentation of the evaluation method of respiration and heart beat enabling us to forecast the sudden death syndrome. The further object of this invention is to provide evaluation apparatus that enables us to identify the state of infant just before sleep-apnea by calculating the correlation coefficient between respiration and heart beat automatically as well as to forecast such a state.

The evaluation method of respiration and heart beat by this invention consists of the following procedures: calculation of waveform interval variation from cardio-electric information of an organism; calculation of envelope curve information of waveform from respiratory information of the organism; sampling of this envelope information at the waveform interval of cardio-electric information; calculation of cross correlation between the waveform interval variation of the aforementioned cardio-electric information and sampled envelope information of respiration; and the evaluation of advancement-retardation relation between respiration and heart beat at the point of the highest correlation coefficient.

Further, the apparatus for evaluation of respiration and heart beat by this invention consists of the following means: a means for detecting cardio-electric and respiratory information as a waveform; a means for calculating the change of corresponding waveform interval from the cardio-electric waveform detected by the above-mentioned means; a means for calculating the envelope information from the respiratory waveforms detected by the above-mentioned detecting means by sampling them at the waveform interval of the above-mentioned cardio-electric waveform; and a means for analyzing the correlation between the change of waveform interval calculated by these calculating means and the envelope information.

The evaluation method of this invention enables us to analyze the change of respiration at the same scale as the change of waveform intervals by sampling the envelope information of respiratory information at the waveform interval of cardio-electric information. Then, by elucidating the cross correlation between the change of waveform intervals of cardio-electric information and the sampled envelope information, the advancement-retardation relation between respiration and heart beat at the point of the highest correlation coefficient can be analyzed. In the normal state of a newborn, respiration shows an advancement of several beats to heart beat, and just prior to the phase of sleep-apnea the relation of respiration to heart beat shows the change from the advancement of several beats to retardation or advancement of several ten beats. This can be attributed to the fact that as the higher order center and autonomic nerve system of a newborn are underdeveloped, the stimulus conduction in the circulatory system does not work correctly. Besides the state of sleep-apnea depends mutually upon the following two factors: the incorrect stimulus conduction in the circulatory system caused by the underdevelopment of the high-order center and autonomic nerve system and the circulatory disturbance due to apnea, and the retardation of negative feed back between the respiratory center and chemical receptor. After the sleep-apnea episode the same results as the normal state can be obtained This can be attributed to the fact that the stimulus conduction in the circulatory system is going back to its original normal state. This correlation between respiration and heart beat permits us to identify the timepoint immediately before the start of a sleep-apnea episode and to forecast sudden death syndrome.

Also, the evaluation apparatus of this invention performs the above-mentioned method, detects respiration and heart beat, and analyzes their correlation. This enables us to be informed of sleep-apnea in a newborn directly before its episode and to forecast sudden death symptom.

DESCRIPTION OF PREFERRED EMBODIMENTS

Figure 1:
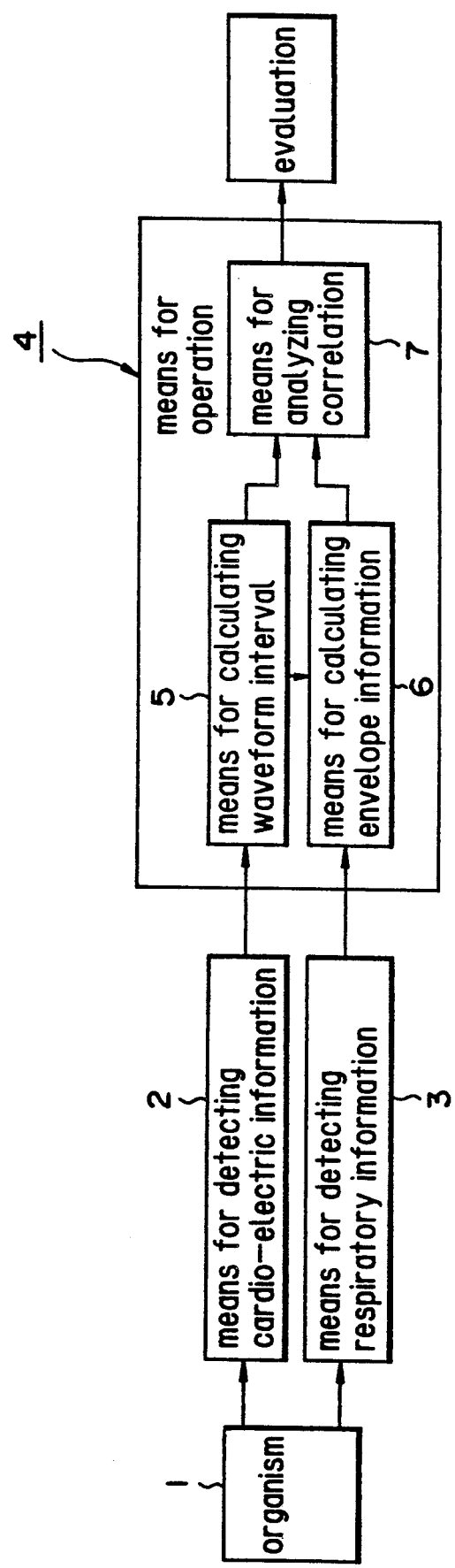
FIG. 1 is a block diagram showing the principle of evaluation of respiration and heart beat relating to an example of this invention.

Referring to FIG. 1, an organism 1 is an information source, from which cardio-electric and respiratory information can be obtained, for example, a newborn. Apparatus 2 for detecting cardio-electric information can detect a cardio-electric waveform from an organism 1 as a potential change. Apparatus 3 to detect respiratory information can detect a respiratory waveform from an organism 1 as a potential change. Apparatus 4 is a microcomputer and the like by which correlation between cardio-electric and respiratory information can be calculated. This calculating means 4 is composed of means 5 for calculating variation of the waveform interval of cardio-electricity, a means 6 for calculating envelope information of the respiratory waveform and a means 7 for analyzing the correlation between the change of waveform interval and envelope information.

Figure 2:
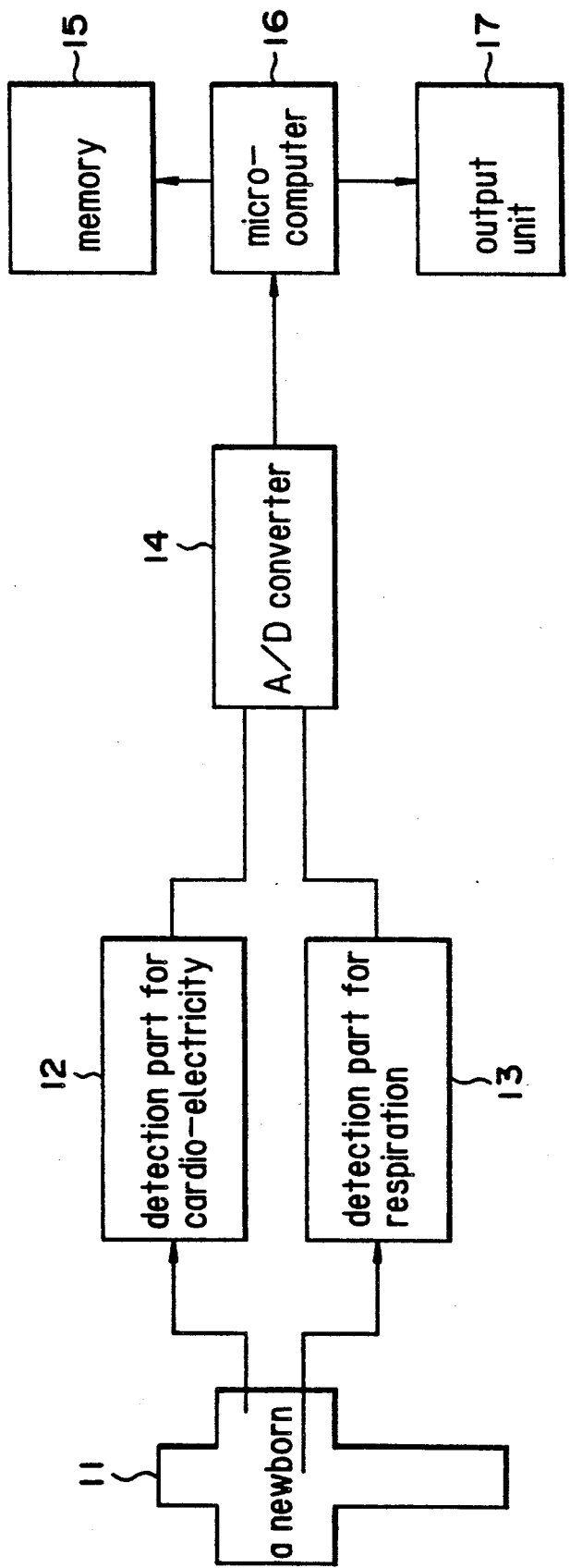
FIG. 2 is a block diagram showing the constitution of evaluation apparatus of respiration and heart beat according to the principle shown in FIG. 1.

Referring to FIG. 2, a newborn 11 is connected to a detector 12 of cardio-electricity and a detector 13 of respiration, which in turn are connected to an A/D converter 14 that converts analog data into digital data. A hard disc memory 15 with about 20 megabytes memory capacity records bulk data, and a micro-computer 16 reads out the data in the memory 15 and computes and processes according to a given program. Output equipment 17 may include a display, X-Y plotter and printer.

In above-mentioned evaluation apparatus of respiration and heart beat the information from a subject, newborn 11, is detected by a detection device for cardio-electricity 12 and a detection device for respiration 13. Then, in order to analyze on a micro-computer 16, the detected information is recorded on a memory 15, 20M hard disc as a form of random access file. The merit of using a random access file is that it has a large capacity of data filing. The data filed on a hard disc is read out as needed and processed by a micro-computer 16.

Here, such information from organisms as cardio-electricity must be recorded for a long time continuously. Usually, data are memorized on main memory and recorded on disc. But, it is impossible to record long-term data. Thus, in the apparatus of this example DMA (direct memory access) a data transfer method is applied. In this method data are transferred in parallel to a disc, while A/D conversion is being carried out. Hereafter, I will explain the method in detail.

As the method for recording data continuously on disc, after preparing the data in a buffer memory of a given capacity, it is as a whole recorded. On the other hand, A/D conversion is carried out at a constant interval, and the data is stored at a constant rate. Thus, the buffer having twice the capacity as the capacity of data transferred en bloc on disc is prepared. In regard to A/D conversion and the transfer of its results, they are repeatedly recorded from the beginning of the buffer to its end by means of hardware, and when the half capacity becomes full, they are transferred to a disc in parallel with A/D-conversion by software. In this method it is possible to record continuous data until the disc is full. As the over-all recording speed comprising seek time, head positioning time, latency time and checking time for buffer filling, must be faster than the sampling speed for A/D conversion, the maximum of sampling frequency may be limited. In this example 1 KHz is used as the sampling frequency. Then, I will demonstrate concretely how the checking on half filling of the buffer can be carried out.

In the A/D converter 14, after transferring half capacity of the buffer to disc, the last one byte is changed to null, and if on reading out and checking the byte, its value changes to a value other than zero, it is considered that the next data has been already recorded in this place. But, because in the A/D conversion results all bits can be zero, one digital input is selected and its input terminal should be open. Then, the bit input will be one, thus if the bit shows 1 on checking, the next data may be considered already to be recorded. By means of the above-mentioned method DMA transfer can be realized.

Figure 3:
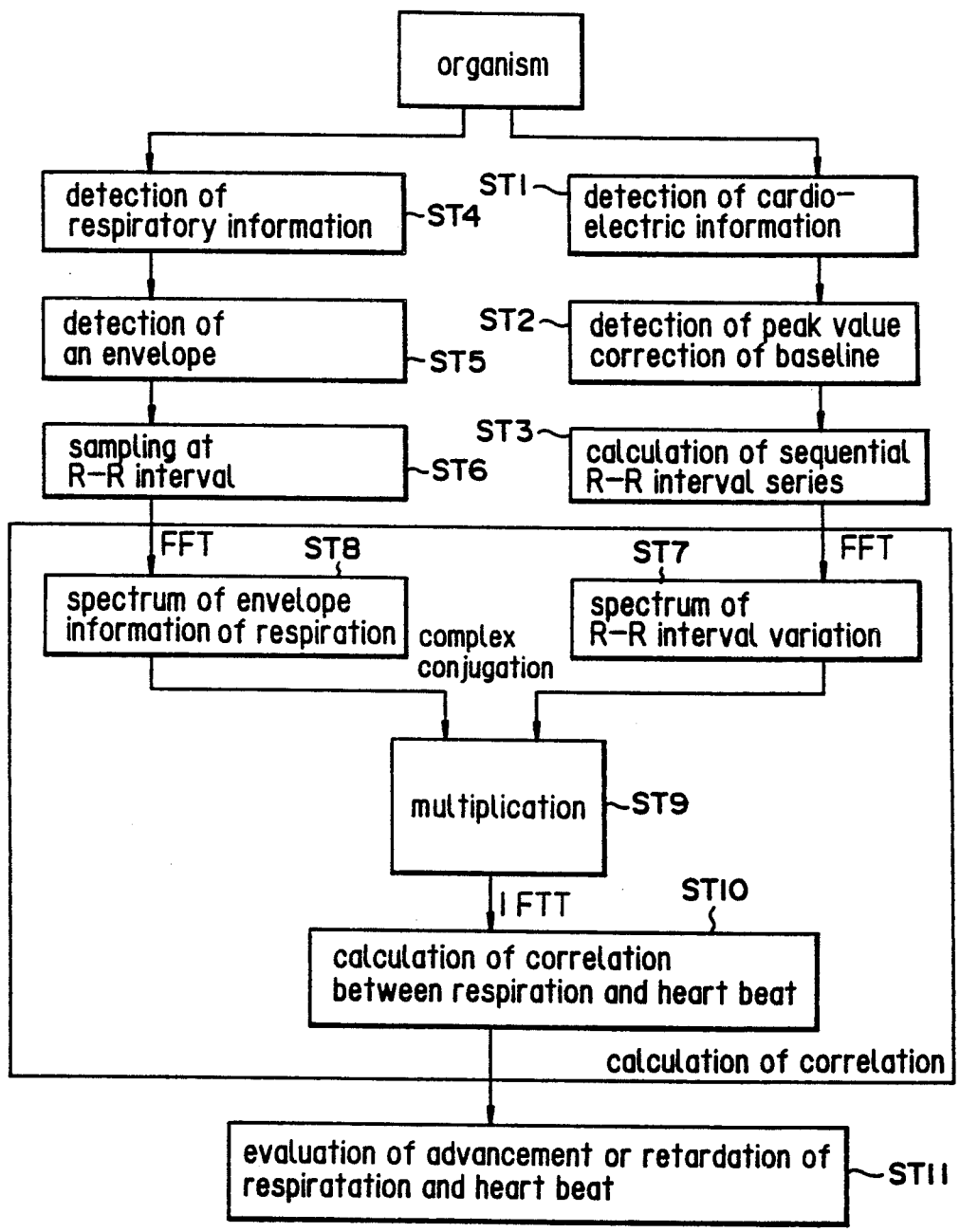
FIG. 3 is a flow chart showing evaluation procedures of respiration and cardio-electricity in this example.

Referring to FIG. 3, Step 1 is the detection of cardioelectric information (heart beat) from the body; Step 2 is the detection of peak (R) value of cardio-electric waveform and the correction of baseline; Step 3 is the calculation of variation of the R—R interval. On the other hand, simultaneously, Step 4 is the detection of respiratory information from the body, Step 5 is the detection of respiratory waveform, Step 6 is the Fourier transform of the sequential change of R—R interval. Then, in Step 9 the multiplication of both frequency spectra obtained in Steps 7 and 8 are performed; in Step 10 the correlation between respiration and heart beat is calculated by means of the reverse Fourier 15 transform. And, in Step 11 the advancement-retardation-relation in respiration and heart beat is evaluated by means of the correlation value obtained in the Step 10.

Next, the sequential variation of the R—R interval and the method of calculation of correlation will be explained in detail.

(1) Chronological series of interval variation

The heart performs a pumping action that causes blood to be circulated in the body by receiving blood of lower pressure from veins and delivering it towards arteries at higher pressure. This action is mainly effected by the contraction of cardiac muscles of ventricular wall. As the electric excitement, that is, activity potential precedes contraction of a bone muscle, also the activity potential does myocardial contraction. As the voluminous muscle fibers show the systematic electric excitement in the determined sequence, the accompanied activity current flows through the all-over body and gives a considerable potential change. The electrocardiograph (ECG) is the change recorded at the body surface.

Figure 4:
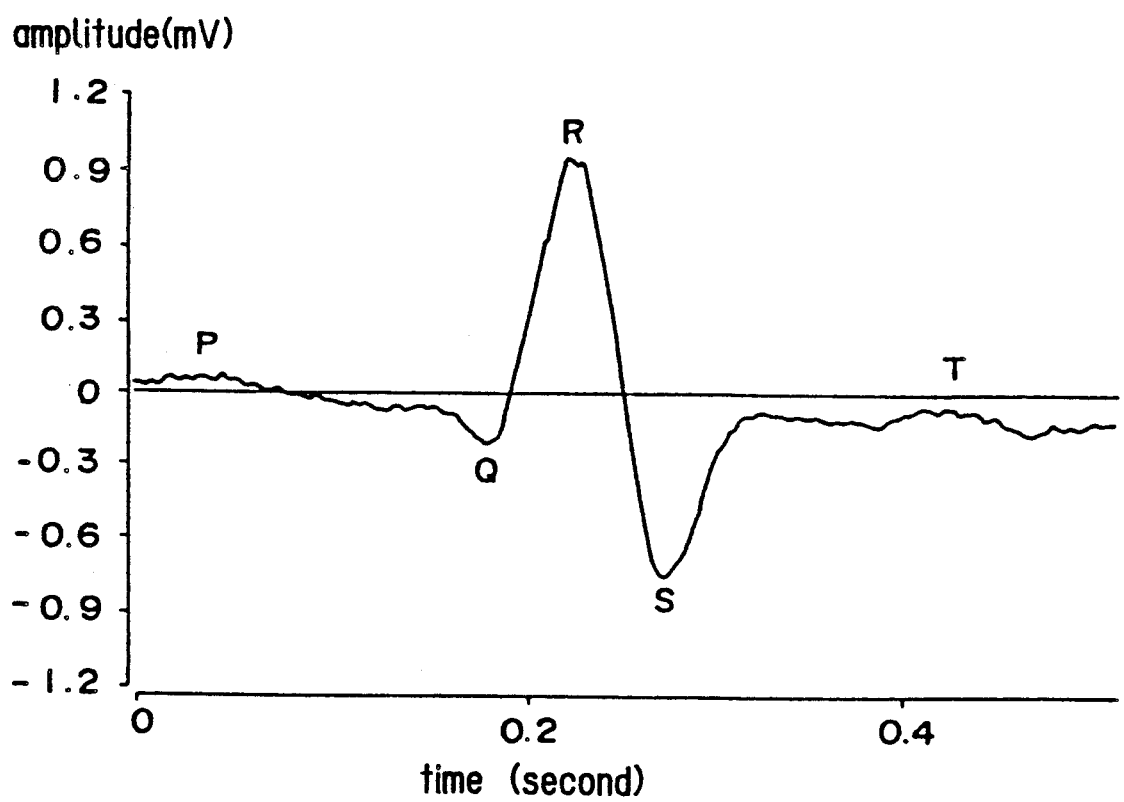
FIG. 4 shows the PQRST of an ECG.

FIG. 4 shows the PQRST of an ECG.

(a) Detection of peak value

Figure 5:
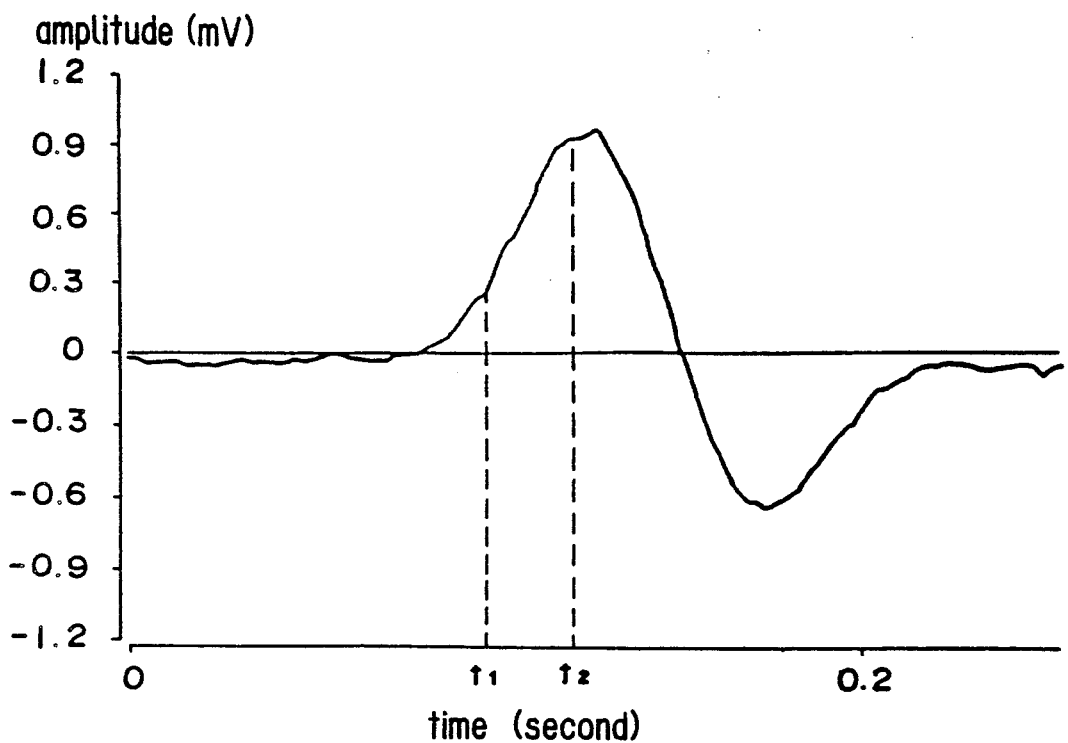
FIG. 5 shows an ECG quantized at a constant period $\tau$.

The method of peak value detection, which is applied for the data preparation of sequential change of the R—R interval will be explained as follows:

FIG. 5 shows a part of an ECG quantized at a constant period $\tau$.

When this waveform is represented by a function X(t) at t on the time axis, the differential value at two points $t_1$-$t_2$ will be represented in the following equation.

$$\frac{dX(t)}{dt} = \frac{X(t_2) - X(t_1)}{t_2 - t_1} \quad (1)$$

besides, if $t_2 = t_1 + \tau$, equation (1) will be represented in the following equation (2).

$$\frac{dX(t)}{dt} = \frac{X(t_1 + \tau) - X(t_1)}{\tau} \quad (2)$$

Figure 6:
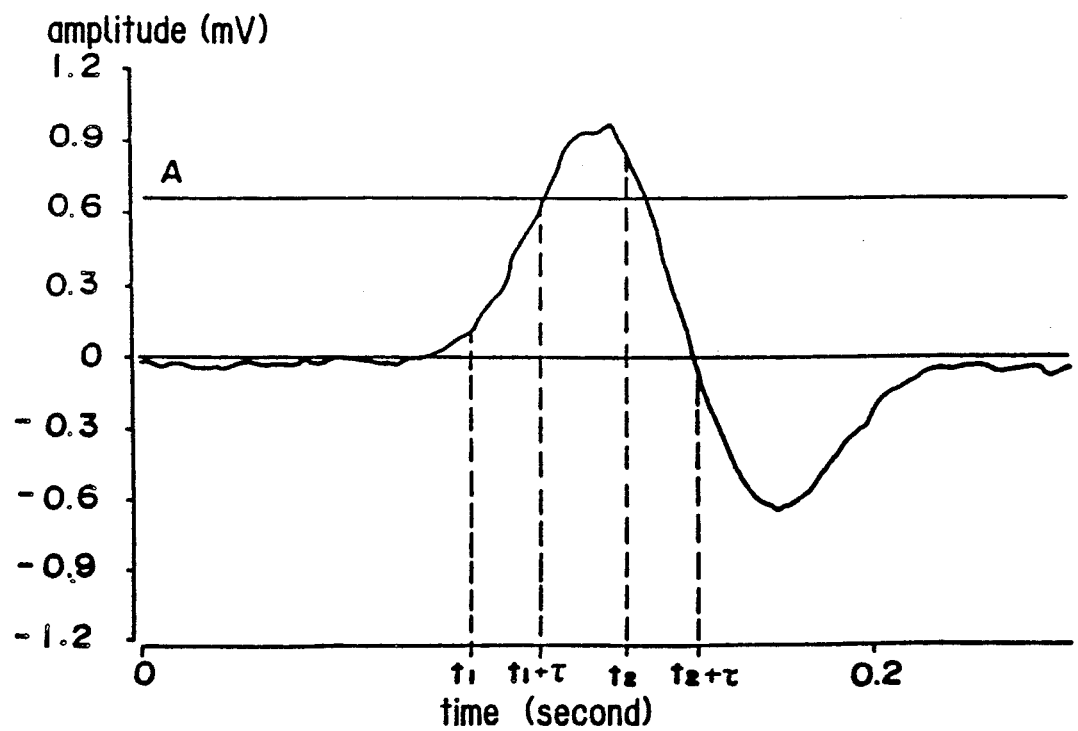
FIG. 6 shows an ECG quantized at a constant period $\tau$.

Then, differentiation at two ranges $t_1$ to $t_1+\tau$, $t_2$ to $t_2+\tau$ ($t_2 \geq t_1 + \tau$) is performed. As shown in FIG. 6, when the peak value is t in $t_1 + \tau \leq t \leq t_2$, the differentiated values of two ranges will be expressed by the following two equations:

$$\frac{X(t_1 + \tau) - X(t_1)}{\tau} \geq 0 \quad (3\text{-}1)$$

$$\frac{X(t_2 + \tau) - X(t_2)}{\tau} \leq 0 \quad (3\text{-}2)$$

Briefly, the point that meets the conditions of equations (3-1) and (3-2) becomes a peak value; the points that meet these conditions are peak values of P,Q,R,S,T. In this example, as a peak value of R-wave is necessary, a constant level A which PQRST-wave does not reach is set and the maximum of a point that meets (3-1), (3-2) and $X(t) \geq A$ is designated as the peak value of R-wave.

Figure 7:
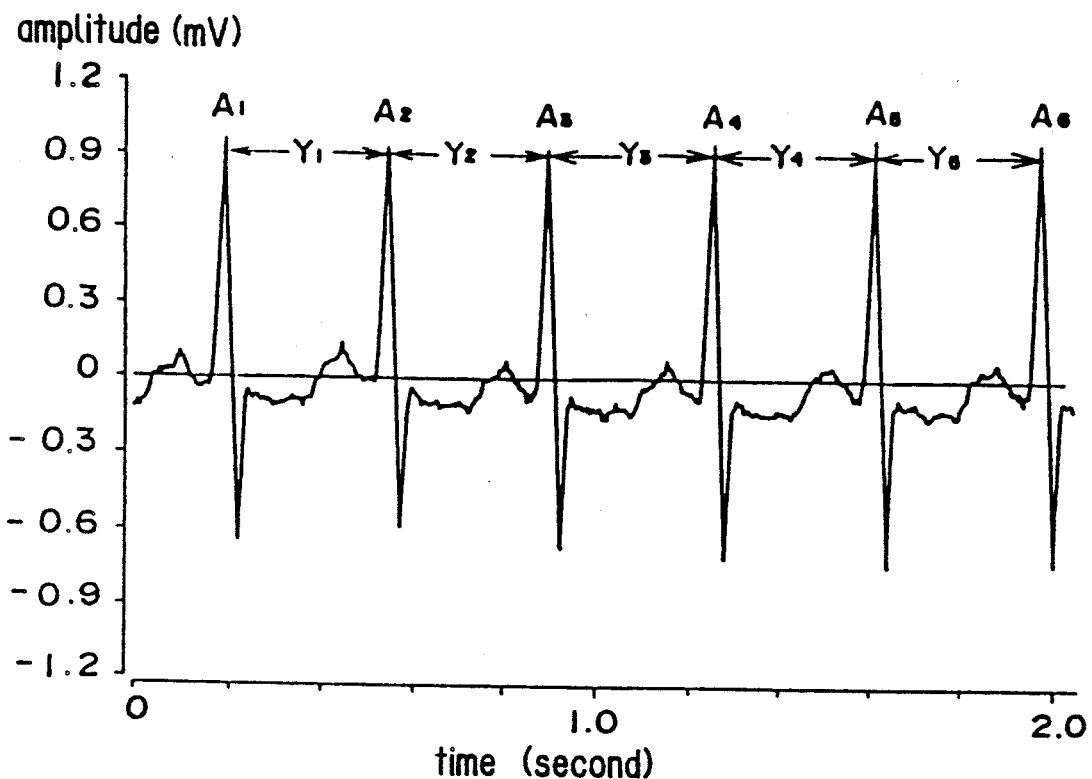
FIG. 7 shows changing an R—R interval.

In FIG. 7, when points of peak value by this procedure are $A_n$, the variation of R—R interval $Y_n$ will be represented by the following equation.

$$Y_n = A_{n+1} - A_n \quad (4)$$

Figure 8:
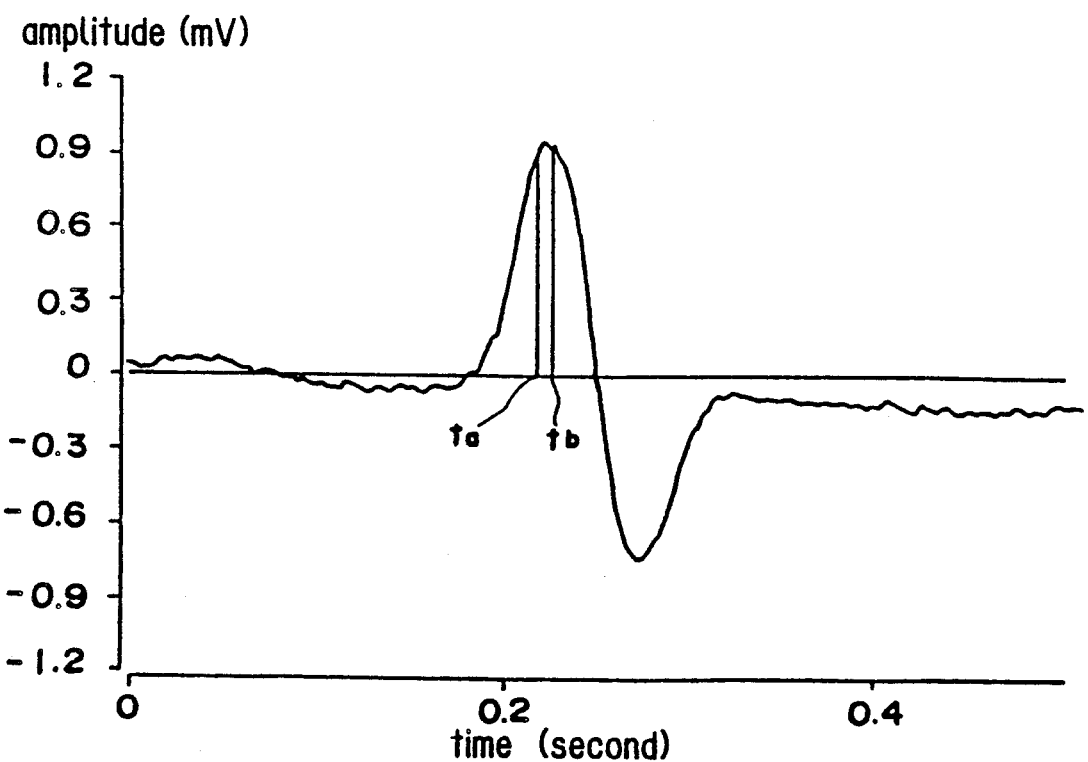
FIG. 8 shows 2 peaks in R waves of an ECG.

In regard to the detection of peak value by means of differentiation, in FIG. 6 the very precise detection is feasible, but in FIG. 8 the points that meet the two equations (3-1), (3-2) and $X(t) \geq A$ are two points, $t_a$ and $t_b$; thus it is impossible to detect the precise peak. In the following, other methods will be explained, considering these points.

Figure 9:
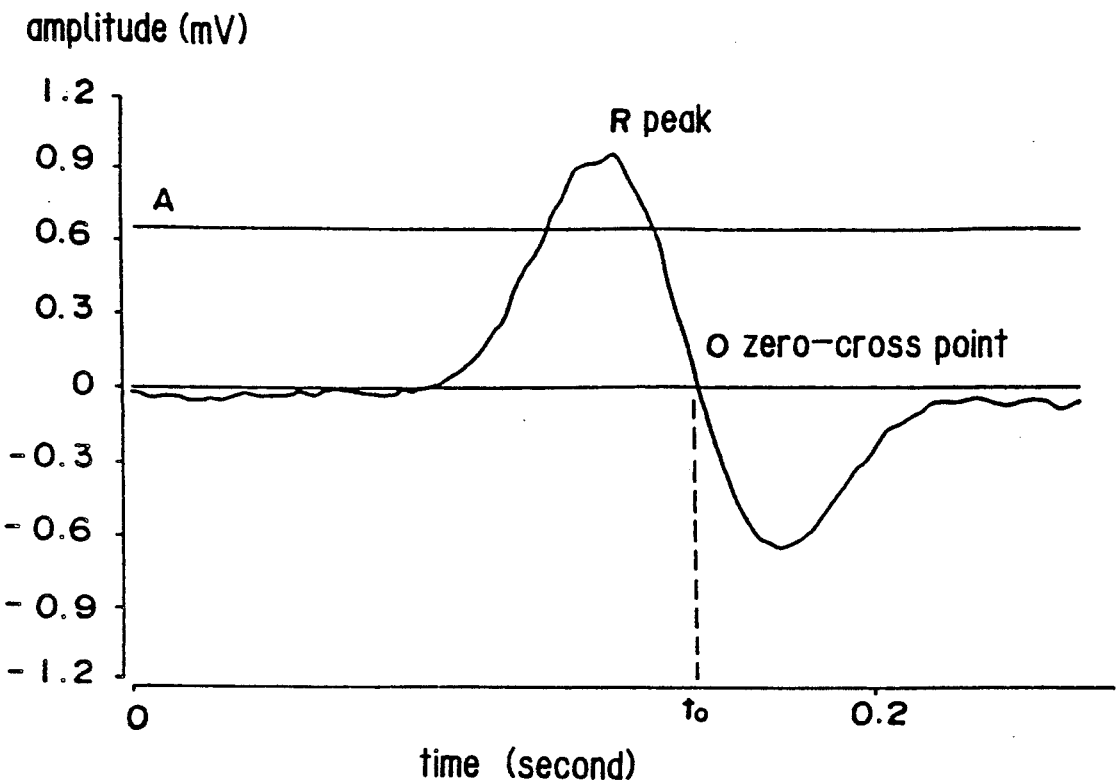
FIG. 9 shows a zero-cross point.

The data necessary for the sequential time analysis is not a peak value, but a time interval of peak value points. Thus, when peak points of R-wave are substituted by zero-cross points, as the R—R interval is discussed, zero-cross points, that are substituted for R-wave peaks detect the points between R—S waves nearest to R-wave. Concrete detection of the zero-cross point is carried out in the same fashion as the differentiation method by determining a constant level A and $X(t) \geq A$. This zero-cross method is shown on FIG. 9. In this figure, if the zero-cross point is $B_n$, sequential data of zero-cross intervals $Y'_n$ will be represented by the following equation:

$$Y'_n = B_{n+1} - B_n \quad (5)$$

Figure 10:
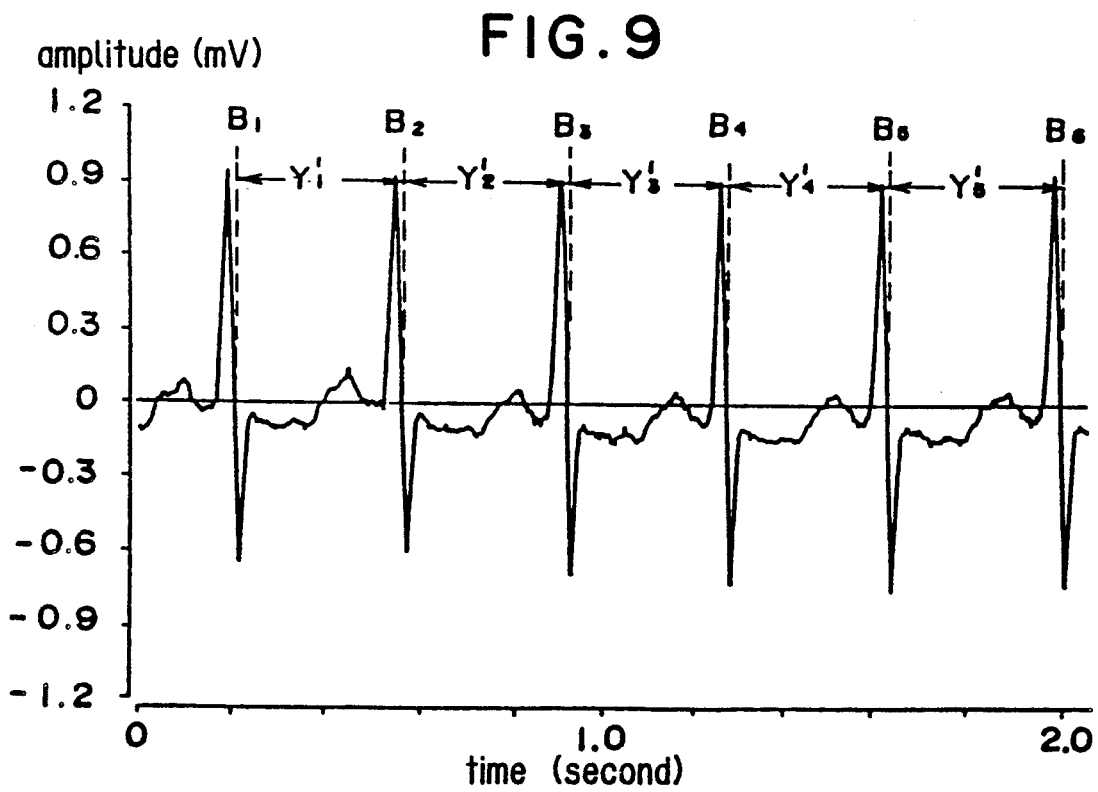
FIG. 10 shows changing an R—R interval of a cardio-electric waveform on the base of zero-cross point.

FIG. 10 shows sequential change of zero-cross point intervals.

(b) Correction of baseline

The real waveforms of ECG, EEG, respiration etc. are not changing on the constant baselines, the baseline itself is changing; thus it is difficult to detect the R—R interval precisely with ECG and so on. In this example, the correction of baseline is carried out without using a band-filter by means of calculation with Fourier spectral analysis.

Figure 11:
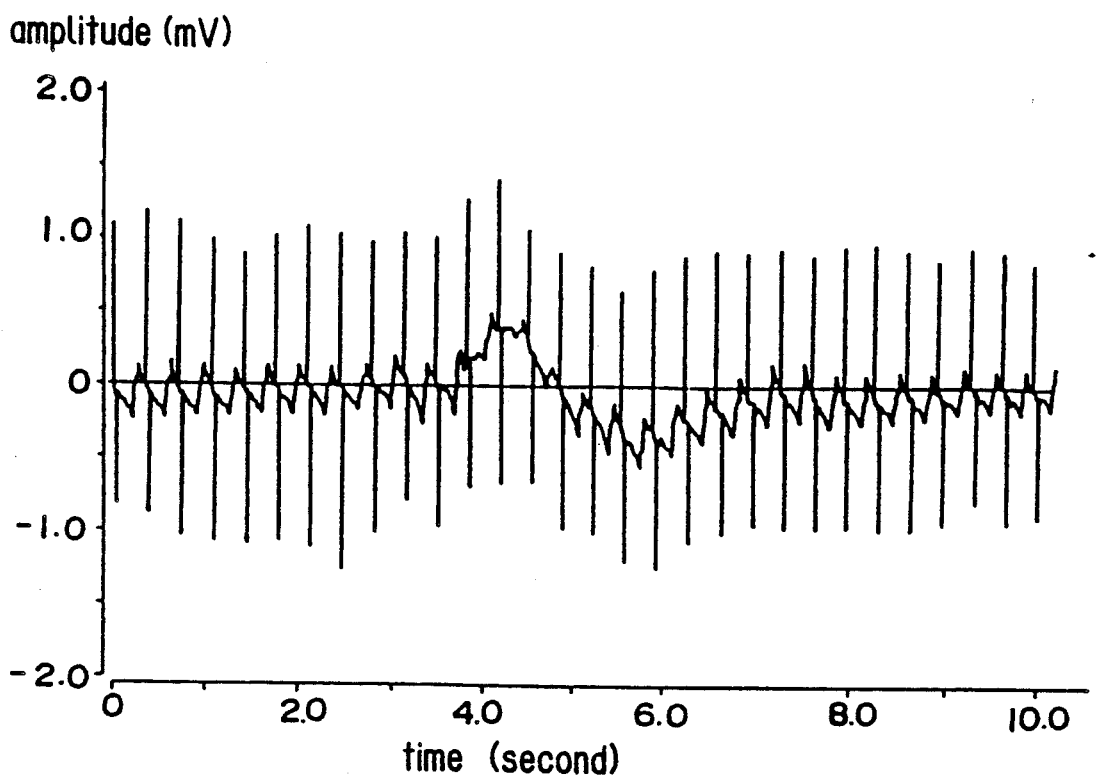
FIG. 11 shows a swaying baseline.
Figure 12:
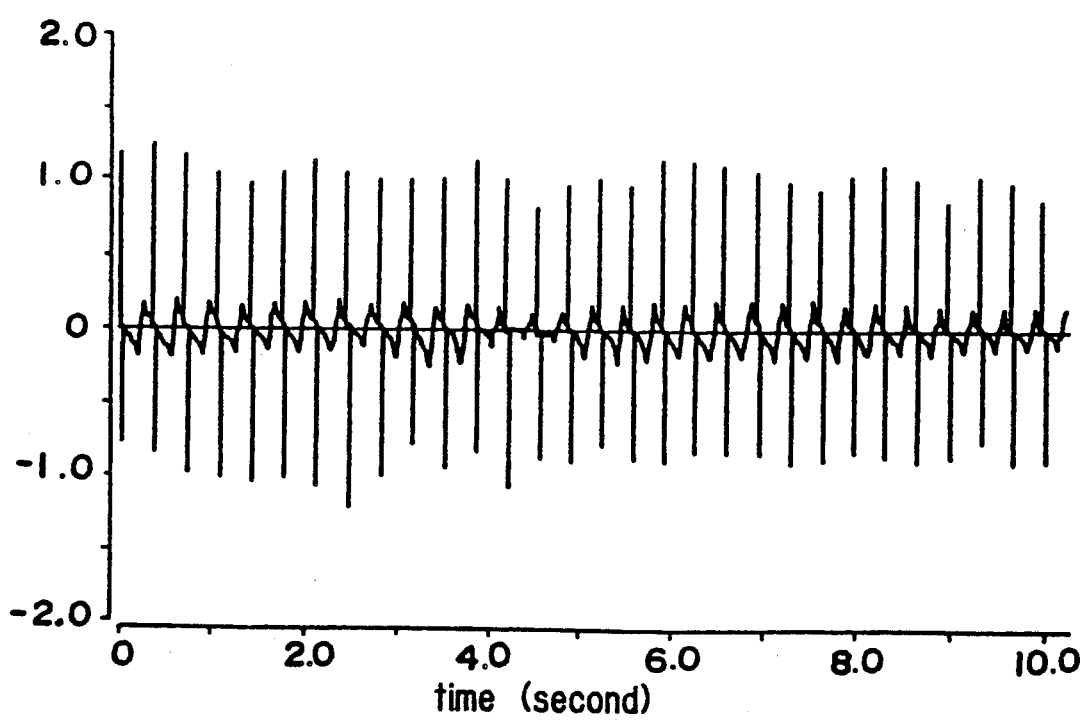
FIG. 12 is a baseline-corrected figure obtained from FIG. 11.

In the Fourier spectral analysis of a cardio-electric waveform the frequency of baseline swaying appears as spectral information of lower frequency than the frequency of the cardio-electric waveform itself. FIG. 11 shows a swaying baseline. Thus, the reverse Fourier transform is performed, eliminating these components of lower frequencies and retaining the components of frequencies of the cardio-electric waveform. FIG. 12 is a baseline-corrected FIG. 11. The cardio-electric waveform itself shows almost no change, also the R—R interval remains unchanged. Further, as this method consists of fast Fourier transform and reverse FFT, the processing time becomes relatively shorter.

Figure 13:
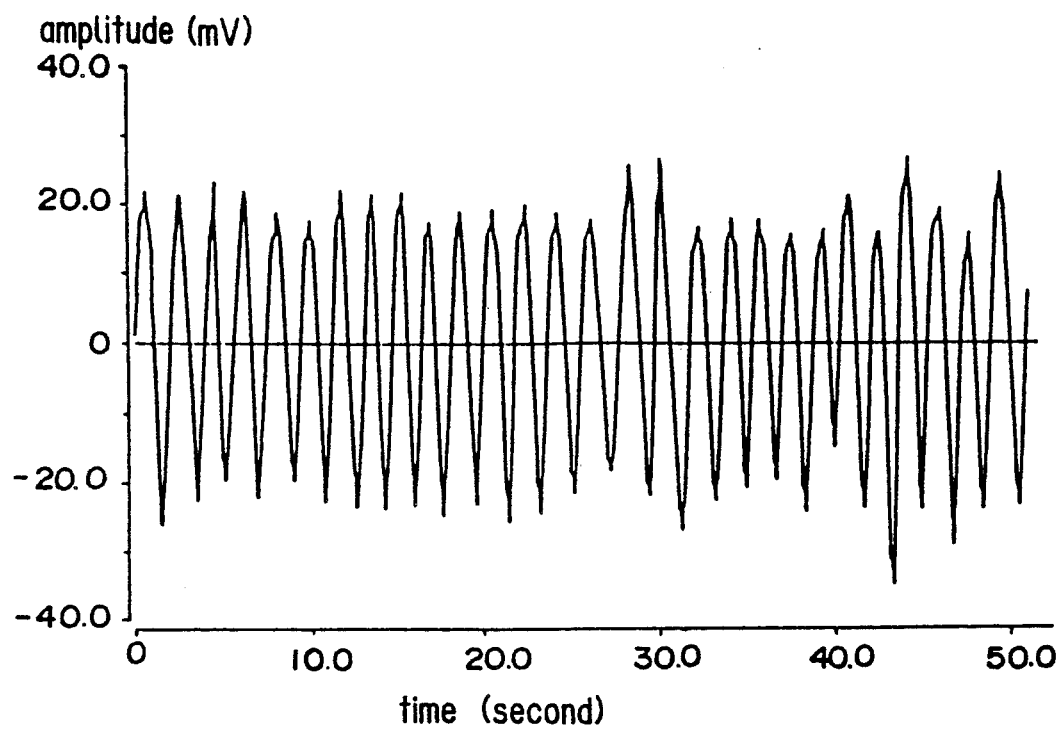
FIG. 13 shows a respiratory waveform.

In the sequential data of the R—R interval on the corrected baseline, if the number of data is N, measuring time T, the ordinate shows the change of the R—R interval, the abscissa a constant interval T/(N−1). Also, FIG. 13 shows a respiratory waveform.

Figure 14:
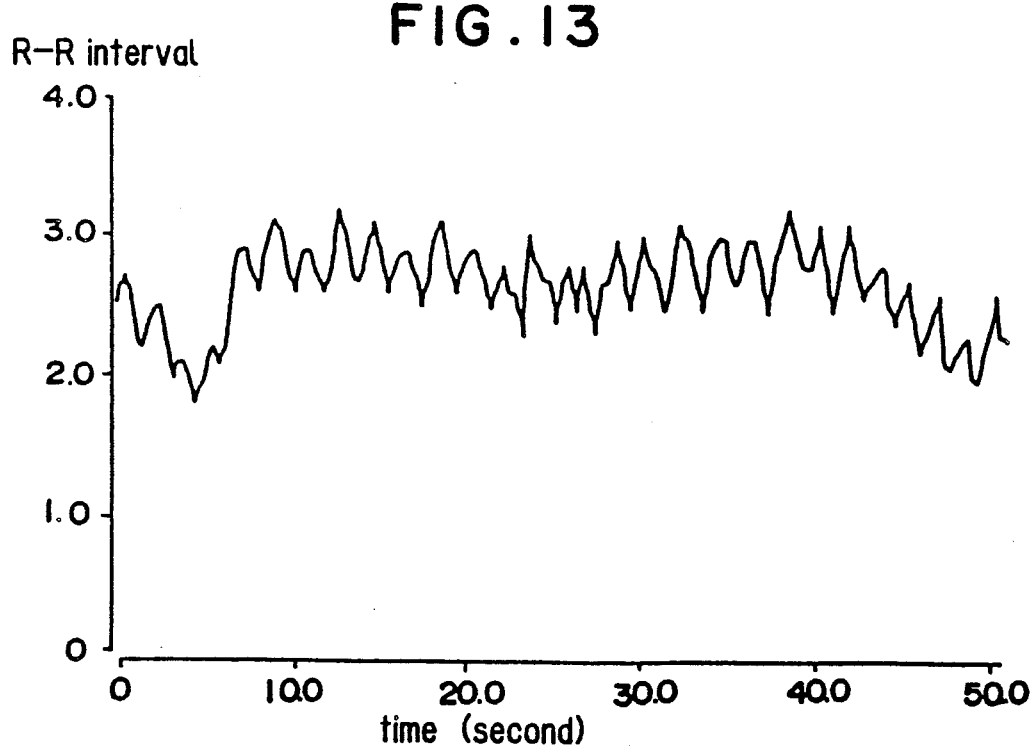
FIG. 14 shows the sequential change of an R—R interval at the time point when the respiratory waveform was measured.

FIG. 14 shows the sequential change of the R—R interval at the time point when the respiratory waveform was measured.

(2) Correlation between respiration and cardioelectricity (a) Fast Fourier transform Fast Fourier transform (FFT) belongs to a discrete Fourier transform and is an algorithm for obtaining rapidly the following discrete Fourier transform formula:

$$W^{nk} = \exp(-j2\pi nk/N) \qquad (6)$$

$$G(n/N) = \frac{1}{N} \sum_{k=0}^{N-1} g(k) W^{nk} \qquad (7)$$

Hereafter, the frequency-thinned-out FFT will be explained.

Sampling and digitization are necessary for the Fourier transform on a micro-computer. At first, about sampling, such a sampling frequency is selected, as it becomes the Nyquist frequency that retains the necessary information of data. The analog data is represented at a constant frequency $\tau$.

(b) Frequency-thinned-out FFT

Let us suppose that data number of sample value N is, for example, g(n). At first, g(n) is divided into the former* half of series e(n) and the latter half of series h(n).

$$e(n) = g(n) \quad (0 \leq n \leq N/2 - 1)$$

$$h(n) = g(n + N/2) \quad (0 \leq n \leq N/2 - 1)$$

Then, the discrete Fourier transformer $G_k$ is given by the following formula:

$$G_k = \sum_{n=0}^{N-1} g(n) W^{nk} \qquad (8)$$

$$G_k = \sum_{n=0}^{N/2-1} \{e(n) W^{nk} + h(n) W^{nk(n+N/2)k}\} \qquad (9)$$

$$G_k = \sum_{n=0}^{N/2-1} \{e(n) + h(n) W^{nk/2}\} W^{nk} \qquad (10)$$

Also, from the formula (6)

$$W^{nk/2} = \exp(-j\pi k) \qquad (11)$$

$$= \begin{cases} 1 \\ -1 \end{cases}$$

From this, if the spectrum of the even numbered sequence of $G_k$ is designated $G_{2-k}$, the odd numbered $G_{2k+1}$, the following relations are derived:

$$G_{2k} = \sum_{n=0}^{N/2-1} \{e(n) + h(n)\} W^{2nk} \qquad (12)$$

$$G^{2k+11} = \sum_{n=0}^{N/2-1} \{e(n) - h(n)\} W^{n(2k+1)} \qquad (13)$$

$$= \sum_{n=0}^{N/2-1} \{(e(n) - h(n)) W^n\} W^{2nk} \qquad (14)$$

These formulas show that in case of N=8 the spectra of even numbers, $G^0$, $G^0$, $G^4$ and $G^6$ can be derived by the discrete Fourier transform consisted of N/2=4 data of $\{e(n)-h(n)\}$. Similarly, the spectra of odd numbers, $G^1$, $G^3$, $G^5$ and $G^7$ can be obtained from the Fourier transform consisted of N/2=4 data of $\{e(n)-h(n)\}$ $W^n$. Thus, the half amount of calculation enables us to perform the discrete Fourier transform. In case of $N=2^L$ the necessity of $N^2$ multiplications can be reduced to 2N log 2N times.

(c) Time window and frequency spectra

As in digital processing an infinitely large amount of sample sequence cannot be processed, real calculation must be performed on the cut-out part of the sequential waveform samples. Favorably, in FFT this cut-out part should correspond with just one or several cycles, but this correspondence cannot be easily realized because of the limitation of the power of two. Thus, the beginning and end of the cut-out may have effect on the spectral characteristics. In order to reduce this effect the data through time window should be analyzed. The time window not only defines the cut-out range, but also has the roll of weighing function along time axis, that gradually attenuates to null in order to avoid the abrupt change at the both ends of the cut-out. In this example, in order to reduce these effects the time function of a Hamming's window are used as a time window.

If the time for one cycle is T, the Hamming's window h(t) can be expressed by the following equation:

$$h(t) = 0.5 - 0.5\cos(2\pi t/T) \qquad (15)$$

(d) Correlation analysis by FFT

Figure 15:
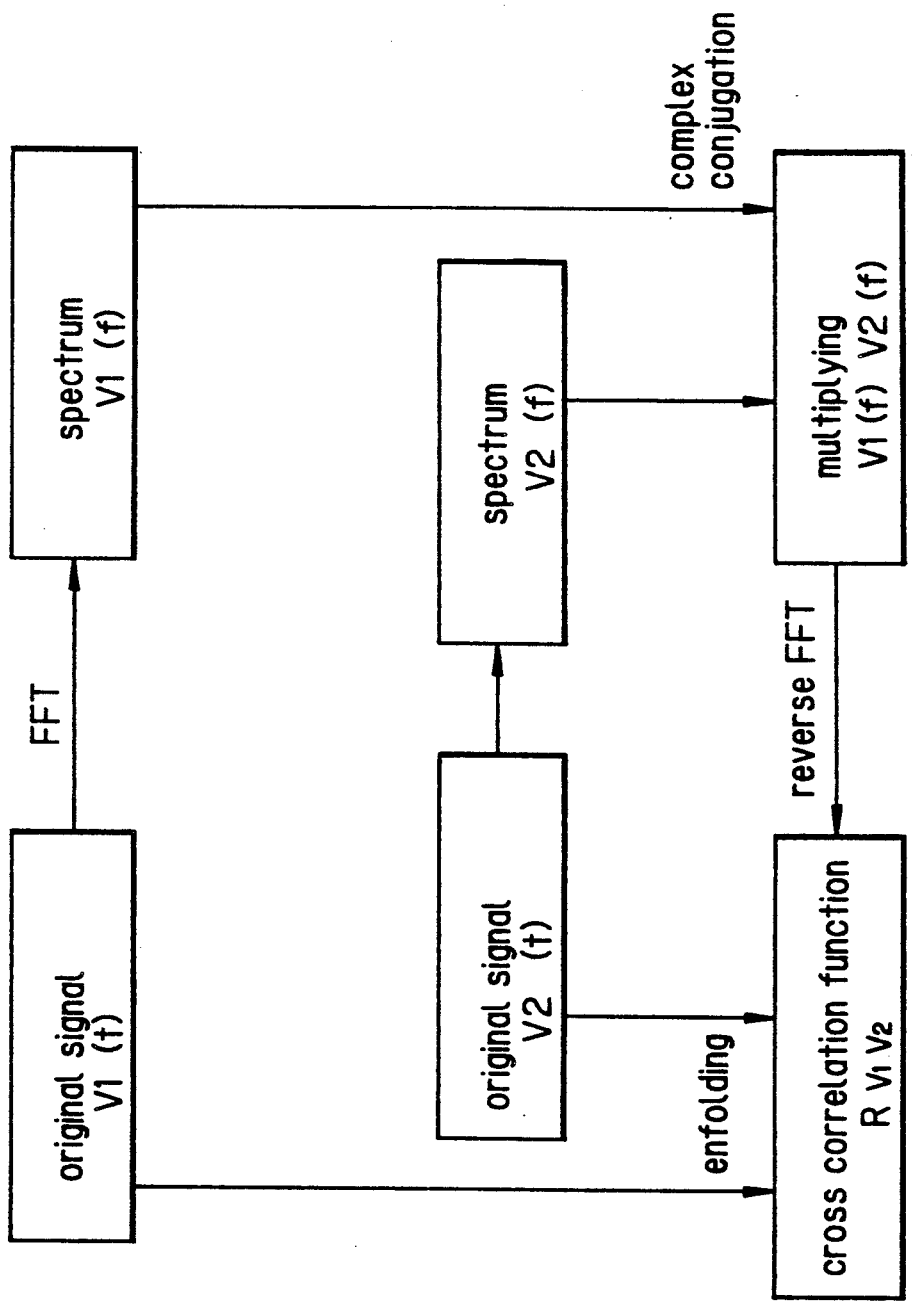
FIG. 15 is a flow chart of the calculation of cross correlation.

FIG. 15 is a flow chart of calculation of correlation. The correlation function R v1v2 ($\tau$) at signals v1 (t) and v2 (t) is defined as the following enfolding operational formula of time range using time difference as a parameter.

$$R\ v1v2\ (\tau) = \sum_{f=0}^{N-1} v1(t)\ v2(t - \tau) \qquad (16)$$

Here, the frequency spectrum of v1(t) and v2(t) is v1(f) and v2(f), respectively. Then, correlation function R v1v2(t) is represented as the following product of frequency ranges.

$$R\ v1v2\ (\tau) = \sum_{f=0}^{N-1} v1(f)\ v2(f)\ W^f \qquad (17)$$

That is, it is expressed as the reverse Fourier transform of product of v1(f) and v2(f). Therefore, the correlation function between v1(t) and v2(t) can be derived by the Fourier transform of v1(t) and v2(t) respectively and the reverse Fourier transform of the product of each frequency range.

(e) Correlation between sequential R—R interval and respiration

In this example the correlation is estimated by FTF*, but there is a difference in sample numbers during the same measuring period when the correlation between respiration and sequential R—R intervals is estimated. When the respiratory waveform is quantized at the same sampling frequency as that of sequential R—R intervals, its Nyquest's frequency is extremely lowered in relation to the R—R interval series; thus the characteristics of respiratory waveform becomes lost. Here, if the envelope waveform of respiratory waveform is quantified at the same sampling frequency as that of the R—R interval series, the characteristics of respiratory curve will be retained. Then, these waveforms are plotted on the new time axis by setting the sampling time as 1 formally. Then, the envelope of respiratory curve and the R—R interval series can be plotted on the same time axis; thus the correlation will be permitted. Also, in this example before checking its correlation normalization is submitted, considering the effect of difference of amplitude and the symmetry of waveform.

We shall explain the results of analyzing heart beat and respiration by means of the aforementioned evaluation method and apparatus.

FIGS. 16 to 19 show the results of analyzing the correlation between respiration and heart beat in newborn. Here, the phase of correlation is based on respiration, and these figures show that the correlation value is the highest at the point ±1 in the correlation.

Figure 16:
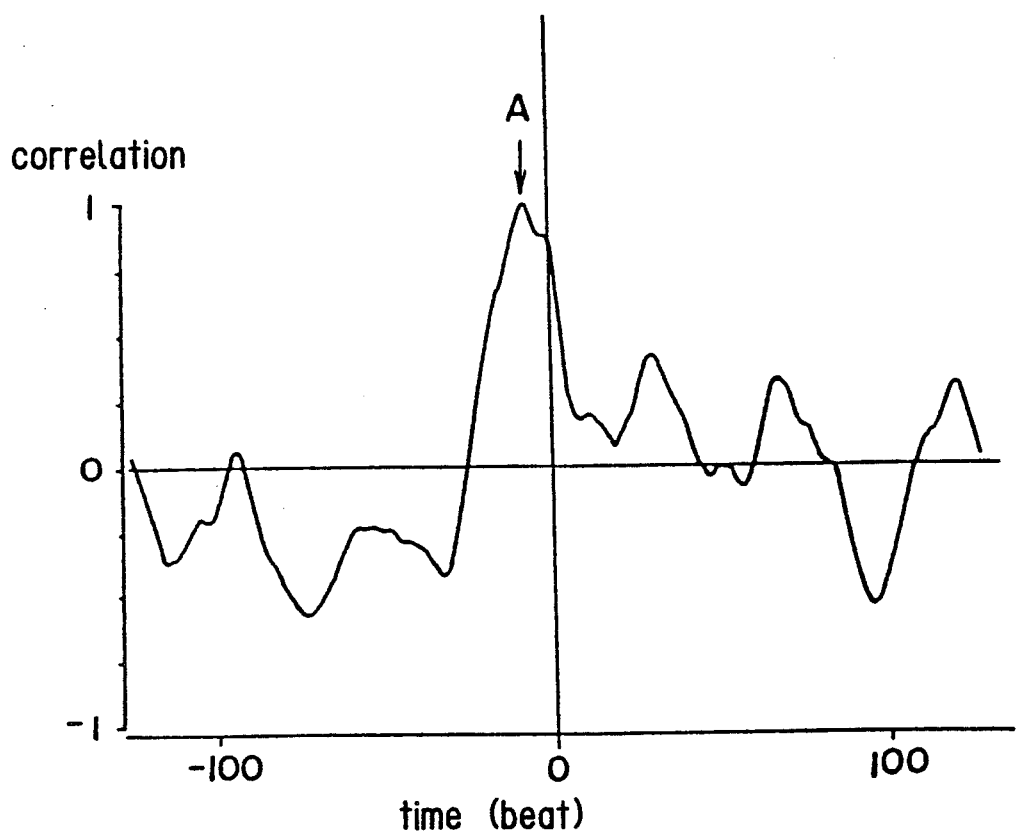
FIG. 16 shows the mutual relation between respiration and heart beat in a normal state.

FIG. 16 shows the mutual relation between normal respiration and heart beat. This figure shows that respiration has the advancement of several beats to heart beat at the A arrow showing the highest value of correlation.

Figure 17:
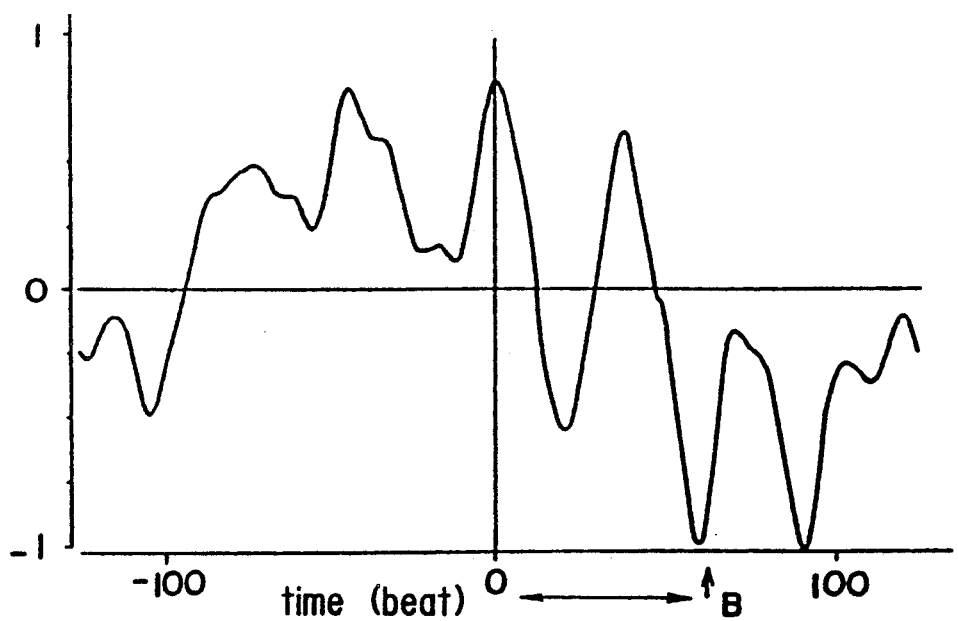
FIG. 17 shows the mutual relation between respiration and heart beat several minutes before the occurrence of sleep-apnea.

FIG. 17 shows the mutual relation between respiration and heart beat several (five to six) minutes before the phase of sleep-apnea. In this figure it is shown that at the arrow B indicating the highest correlation coefficient, respiration has retardation of several tens beats to heart beat. It can be attributed to that as the high-order center and autonomic nerve system do not develop fully, the stimulus conduction is not performed precisely.

Figure 18:
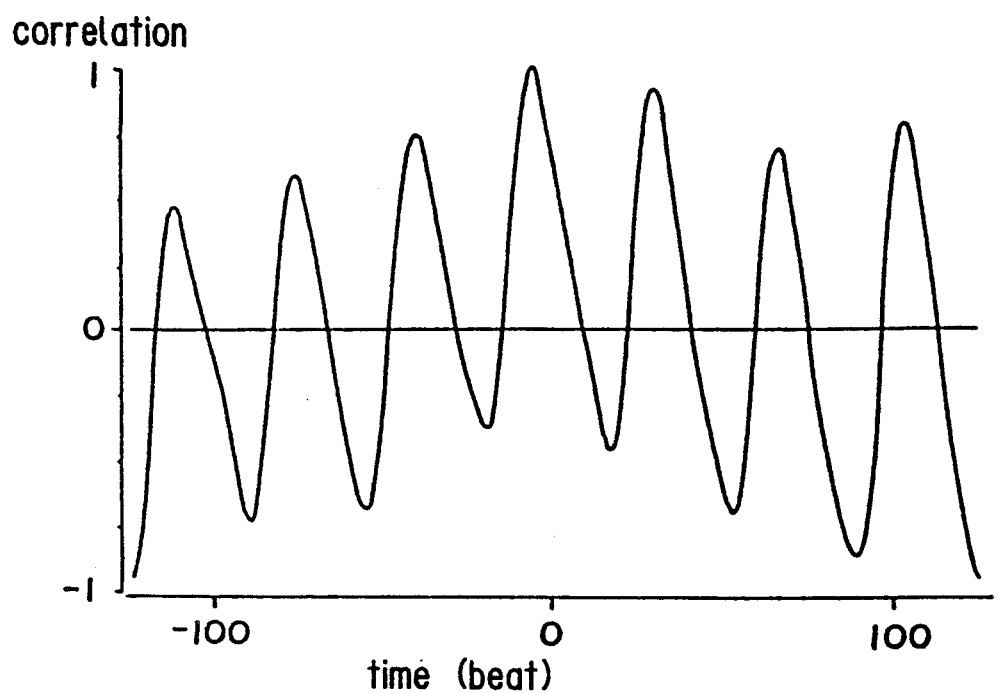
FIG. 18 shows the mutual relation between respiration and heart beat in an episode of sleep-apnea.

FIG. 18 shows the correlation between respiration and heart beat in sleep-apnea. In this figure the correlation value cannot be identified, and it suggests that there may be the advancement or retardation between respiration and heart beat. This can be attributed not only to the fact that the higher center and autonomic nerve system are not fully developed but also to the fact that in apnea the circulatory disturbance occurred.

Figure 19:
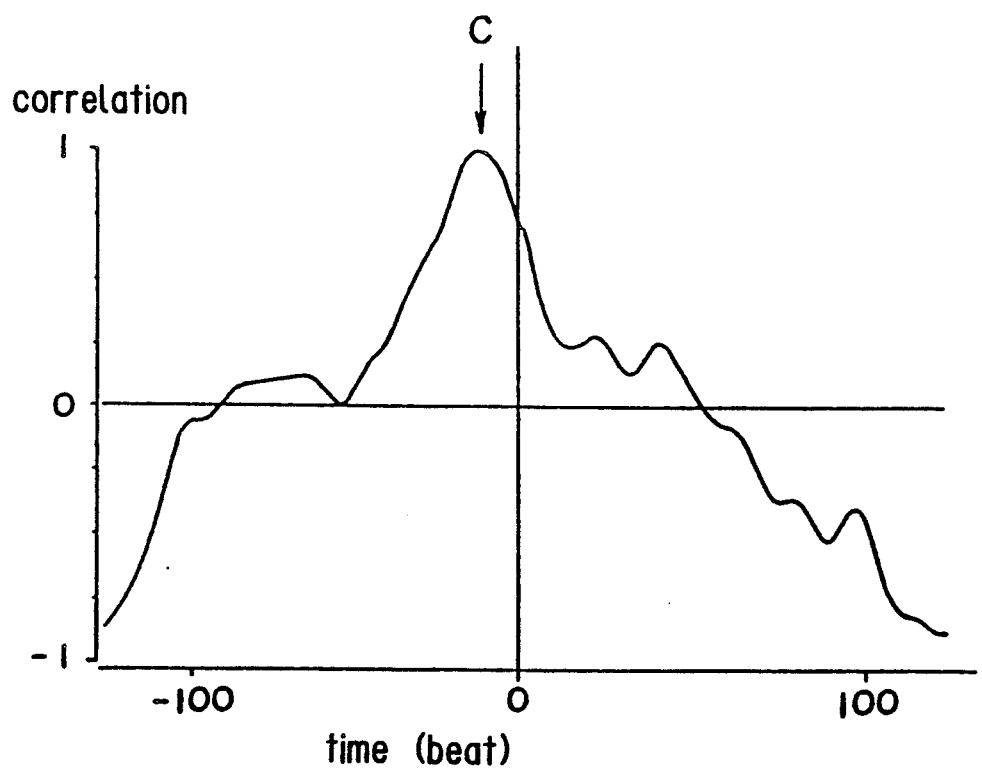
FIG. 19 shows the mutual relation between respiration and heart beat after an episode of sleep-apnea.

FIG. 19 demonstrates the mutual relation between respiration and heart beat after the sleep-apnea.

This figure shows that at the arrow C of the highest correlation value respiration takes the advancement of several beats. This value is almost equal to the normal value in FIG. 16 and shows that the stimulus conduction in circulatory system is going to recover to normal state.

The above-mentioned analysis results of heart beat and respiration revealed that the mutual correlation changes from a normal state several minutes before a central type of sleep-apnea will occur. By means of this mutual relation between respiration and heart beat, it is possible to forecast sudden infant death syndrome previously. Using an apparatus that can analyze this mutual relation automatically, it becomes also possible to give an alarm several minutes before the appearance of sleep-apnea.

Besides, in the above-mentioned examples, a central type of sleep-apnea in newborn was demonstrated, but this invention is not limited to these examples, for example, even in a grown-up with diabetic disturbance of the autonomic nerve system, the above-mentioned diseased patient may show respiratory standstill, and the application of this invention enables giving an alarm for the respiratory arrest.

Further, in regard to cardio-electric information from organisms it is at least sufficient to measure the change of the distance of waveform, and the R—R interval and zero cross point are not limiting factors.

Besides, in the above-mentioned examples correlation was analyzed on the basis of respiration, but it may be also done on the basis of heart beat. In the latter case the relation between advancement and retardation of respiration and heart beat is reversed.

Also, from the cross correlation analyzed by the apparatus of the above-mentioned example the relation between respiration and heart beat in the higher correlation value is calculated automatically, and on the basis of this result the alarm apparatus that can protect a newborn baby by a tone, vibration etc. or notify nurses and physicians of this state before the occurrence of sleep-apnea, can be installed.

Also, in the apparatus of the above-mentioned example by carrying out a correlation analysis under continuous detection of cardio-electric and respiration information for a given period, the apparatus that can always monitor the central type of sleep-apnea in a newborn and so, can be realized.

As explained in detail, the evaluation method of respiration and heart beat and the apparatus for the method by investigating the correlation between respiration and heart beat enable us, for example, to identify the state just before the normal state of a newborn will convert to the state of sleep-apnea and to forecast sudden death syndrome. Further, the automatic calculation of the correlation between respiration and heart beat makes it possible, for example, to identify the state just before the state of sleep-apnea in a newborn as well as to forecast it.

What is claimed is:

1. A method of evaluating respiration and heart beat comprising:

detecting cardio-electric information from an organism;

calculating the variation of waveform interval for heart beat from the detected cardio-electric information;

detecting respiratory information from the above-mentioned organism;

calculating the envelope of the waveform of the detected respiratory information;

sampling said envelope information at a rate equal to the interval of the detected cardio-electric information;

calculating cross correlation between the variation of waveform interval of said cardio-electric information and the sampled envelope information of respiration;

identifying the highest value of cross-correlation; and evaluating the degree of advancement or retardation between respiration and heart beat from said highest value of cross-correlation.

2. Apparatus for evaluating respiration and heart beat comprising:

means for detecting cardio-electric information from an organism;

means for detecting respiratory information from the above-mentioned organism;

means for calculating variation of waveform interval for heart beat from the detected cardio-electric information;

means for calculating the variation of waveform interval for heart beat from the detected cardio-electric information;

means for calculating the envelope of the waveform of the detected respiratory information;

means for sampling the envelope information at a rate equal to the interval of cardio-electric information;

means for calculating cross-correlation between the variation of waveform interval of said cardio-electric information and the sampled envelope information of respiration;

means for identifying the highest value of cross-correlation; and means for evaluating the degree of advancement or retardation between respiration and heart beat from said highest value of cross-correlation.

* * * * *

UNITED STATES PATENT AND TRADEMARK OFFICE
CERTIFICATE OF CORRECTION

PATENT NO. : 5,105,354

DATED : April 14, 1992

INVENTOR(S) : Toshihiro Nishimura

It is certified that error appears in the above-identified patent and that said Letters Patent is hereby corrected as shown below:

Column 3, line 16 for "obtained This" read

-- obtained.  This --.

Column 11, lines 8-10 delete

"means for calculating ... information".

Signed and Sealed this

Eighteenth Day of January, 1994

*Attest:*

BRUCE LEHMAN

*Attesting Officer*     *Commissioner of Patents and Trademarks*